United States Patent [19]

Haerr

[11] 4,096,230
[45] Jun. 20, 1978

[54] METHOD OF FABRICATING A MOISTURE-EXPANDABLE PROSTHESIS

[75] Inventor: Raymond H. Haerr, Cincinnati, Ohio

[73] Assignee: Xomed Inc., Cincinnati, Ohio

[21] Appl. No.: 774,128

[22] Filed: Mar. 3, 1977

Related U.S. Application Data

[62] Division of Ser. No. 608,148, Aug. 27, 1975, Pat. No. 4,034,759.

[51] Int. Cl.² ............................................. B29D 27/00
[52] U.S. Cl. .................................. 264/321; 264/320; 264/324; 264/343
[58] Field of Search ................ 264/320, 324, 343, 321

[56] References Cited

U.S. PATENT DOCUMENTS

| | | | |
|---|---|---|---|
| 2,134,930 | 11/1938 | Reynolds | 264/324 X |
| 2,286,817 | 6/1942 | Knight | 264/324 X |
| 2,433,675 | 12/1947 | Parish | 264/324 X |
| 2,444,528 | 7/1948 | Popper | 264/324 X |

*Primary Examiner*—Richard R. Kucia
*Attorney, Agent, or Firm*—J. Warren Kinney, Jr.

[57] ABSTRACT

A hollow-cylindrical tube of dehydrated, regenerated cellulose sponge material is tightly compressed to provide an elongate member of minimal diameter having sufficient rigidity to be inserted endwise into a body opening where it will, when moistened, expand radially whereby to substantially engage the inner peripheral walls of the opening for securing it against accidental or unintentional dislodgement therefrom. When used in association with an ear canal an axial opening through the expanded member permits sound waves to reach the ear drum.

6 Claims, 6 Drawing Figures

FIG-1
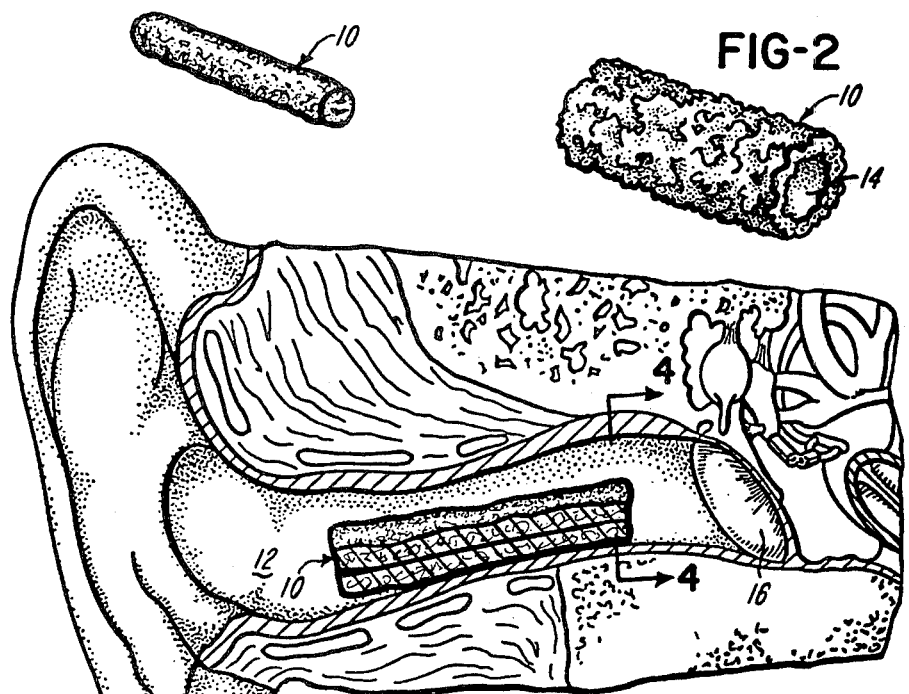
FIG-2
FIG-3
FIG-4
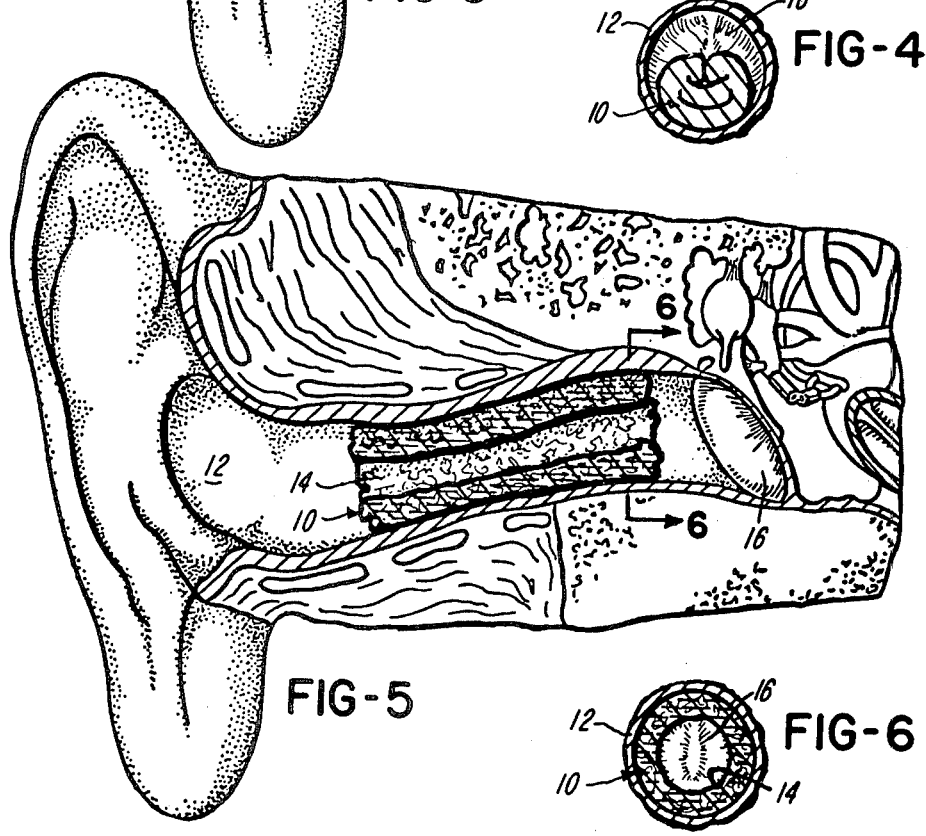
FIG-5
FIG-6

4,096,230

METHOD OF FABRICATING A MOISTURE-EXPANDABLE PROSTHESIS

This application is a Division of Application Ser. No. 608,148, filed Aug. 27, 1975, Now U.S. Pat. No. 4,034,759.

BACKGROUND OF THE INVENTION

1. Field of the Invention

The invention relates to a method of fabricating a dehydrated wick of cellular material which, when hydrated, will rapidly expand radially in an effort to assume its dimensions, prior to compression. The dehydrated wick possesses sufficient rigidity to enable it to be inserted endwise into various body cavities and openings, and when so positioned and hydrated it will rapidly expand whereby to snugly engage the inner peripheral walls of the openings for thereby providing an ideal media for the application of medicant to the walls of the body opening.

2. Description of the Prior Art

The Stephan U.S. Pat. No. 1,210,720, dated Jan. 2, 1917, discloses a surgical cotton splint fabricated into a substantially projectile shaped member by feeding one or more laminae of absorbent cotton to a rewind spindle and placing the cotton toward the axis or along the spindle and beyond the point thereof as the cotton winds upon itself. Each of the cotton layers become so immeshed with the adjacent layer that there is no possibility of the finished product unwinding. By reason of the thinness of the successive layers, the resulting product is a homogenous body of compacted cotton fiber arranged about a center in an elongated pointred form and having sufficient stiffness to be utilized without a handle for use by surgeons, oculists, and nurses for the cleaning of nostrils, ears, etc. The aforesaid splint is not adapted to expand or swell when subjected to moisture.

Applicant is also aware of the following U.S. patents:

Strauss U.S. Pat. No. 2,490,168 which discloses a sinus medication applicator which comprises an elongate, hollow stem having a plurality of lateral openings in open communication with a porous or spongy body member secured to and carried by the stem;

Pietro U.S. Pat. No. 3,506,009, which is directed to a method of making styptic-tipped medical sticks;

Brillant U.S. Pat. No. 3,018,778, which discloses a pellet fabricated from material which expands when it is wet and becomes soft so as to yield and become distorted under light pressure, either to fill or to reach all surfaces of a cavity, or to provide a larger wiping surface and to provide more intimate contact with the surface to be dried or treated, wherein the pellet is fabricated from "sponge rubber", and wherein the pellet is secured to and carried by a thin, flexible applicator of wood, metal or plastic;

Strauss U.S. Pat. No. 2,710,222, which discloses a sponge applicator which is secured to and carried by a hollow tube through which medicant, and other liquids, is supplied to the interior of the sponge;

Davis U.S. Pat. No. 2,510,961, which discloses an ear cleaner which includes a pad of soft, elastic, porous material having good cleansing and scrubbing qualities such as sponge or foam rubber;

Negri U.S. Pat. No. 2,642,065, which discloses a vial containing an analgesic fluid in a protecting container having a substantially fresto-conical shape, from one end of which an absorbent element projects for the purpose of spreading fluid inside of the auditory meatus;

Hartop U.S. Pat. No. 3,865,108, discloses a drug delivery device having a drug containing zone associated with and partially defined by a material which swells on contact with body fluids. When swelling occurs, the pressure on the drug containing zone expels the drug from the device.

BRIEF DESCRIPTION OF THE DRAWINGS

FIG. 1 is a perspective view of a wick of the present invention in a fully compressed condition.

FIG. 2 is a perspective view illustrating the wick of FIG. 1 in a fully expanded condition.

FIG. 3 is a sectional view illustrating the wick of FIG. 1 inserted into the ear canal of a patient.

FIG. 4 is a view taken on line 4—4 of FIG. 3.

FIG. 5 is a view similar to FIG. 3 showing the wick in a fully expanded condition.

FIG. 6 is a view taken on line 6—6 of FIG. 5.

DESCRIPTION OF THE PREFERRED EMBODIMENTS

With particular reference to FIGS. 1, 3, and 4, the numeral 10 denotes, generally, an elongate, substantially cylindrical wick of compressed, dehydrated, cellular material which is sufficiently rigid to be inserted, endwise, into a body opening, such as, by way of example, an ear canal 12, or the like.

The physical characteristics of the wick are such that when hydrated it will expand radially into an elongate, hollow, substantially cylindrical shape, as illustrated in FIGS. 2, 5 and 6.

In those instances in which the dehydrated wick has been inserted into an ear canal 12, the outer surface thereof, will, when the wick has been hydrated, expand radially outwardly whereby to substantially fill and engage the interior surface of the ear canal for thereby precluding its accidental or unintentional dislodgement therefrom.

When utilized, as illustrated in FIGS. 3 and 5, the wick is ideally suited for retaining a medicant in intimate contact with an adjacent surface of the ear canal, and since the member, when expanded is hollow, having an axial opening 14 therethrough, the presence of the wick within the ear canal permits the passage of sound waves to the tympanic membrane 16, whereby the presence of the wick will induce but a minimal hearing impairment to the patient.

Uniformly satisfactory results have been obtained in those instances in which the cellular material comprises fine pore regenerated cellulose sponge as manufactured by the O-Cell-O Division of General Mills, Inc. from sulphite wood pulp.

When the subject members are utilized as an ear wick, as illustrated in FIGS. 1 and 2, the length thereof may approximate ⅜ inch with an outside diameter of ⅜ inch and an inside diameter of from ⅛ inch to ¼ inch.

The compressed, dehydrated, substantialy cylindrical, elongate wick of FIGS. 1, 3, and 4 is fabricated from a dehydrated, cylindrical, elongate, hollow member as illustrated in FIG. 2, such as, by way of example, by the application of a radial, rolling, compressive force to the outer surface of the hollow cylinder of FIG. 2 whereby its outer diameter will be radially compressed to about ⅛ inch — while retaining its overall length of ⅜ inch. During compression the axial opening 14 is completely closed.

The thus compressed, dehydrated, elongate, substantially cylindrical wick is sufficiently rigid to permit it to not only be handled, but to be inserted endwise into a body opening, such as, by way of example, an ear canal. After the wick has thus been positioned it will, when subjected to moisture, such as, by way of example, by the application of a liquid medicant, rapidly expand radially whereby to seek to resume the dimensions, of FIG. 2, which it had before it was compressed to the wick of FIG. 1.

It should, of course, be understood that the fully expanded dimensions of the wick of FIG. 2 will, for any particular application, be determined by the dimensions of the body opening into which the wick is to be inserted. After the fully expanded dimensions have been determined, the fully compressed dimensions of the wick are a function of the wall thickness of the fully expanded cylinder and the degree of compression to which the dehydrated cylinder of FIG. 2 is subjected.

Uniformly satisfactory results have been obtained in those instances in which the outside diameter of the expanded, dehydrated, cellulose sponge material of FIG. 2 approximates 9 mm, and wherein the outside diameter after compression approximates 2 mm. In other words, the diameter after compression is about 20 per cent of the original non-compression diameter of FIG. 2. In other instances the degree of reduction in diameter may vary from 30 to 80 percent.

An object of the compression is to so reduce the outside diameter of the elongate wick or prosthesis such that it may be inserted endwise into a body opening, such as, by way of example, an ear canal 12 without contacting the inner surface of the opening during insertion, in order to eliminate or at least substantially reduce, contact during insertion and thereby minimize the pain which would result by reason of the insertion of an expanded wick member into an inflamed passage of a body opening. Once in place, the radial expansion which occurs in the prosthesis incident to the application of moisture, causes the prosthesis to rapidly, but gently, expand radially to provide contact between its outer surface and the inner surface of the ear canal.

The expansion of a prosthesis, in situ, may be effected by the application of a liquid medicant to the prosthesis of FIG. 3, in which event the medicant, per se, will provide the necessary moisture to produce the desired expansion or, the prosthesis of FIG. 3 may be subjected to moisture, such as sterile water for effecting expansion, as illustrated in FIG. 5, after which medicant may be applied to the fully expanded prosthesis. It will be understood that medicant applied to the prosthesis will be disposed in prolonged contact with the adjacent surfaces of the ear canal, thereby providing a beneficial and prolonged application of medicant to inflamed portions of the ear canal.

It should also be understood that if desired, the outer surface of the compressed prosthesis of FIG. 1 may be suitably coated with paste-like substance, such as salve, ointment, or cream.

While the prosthesis has been described in association with an ear canal, it should be understood that it may be utilized with any body opening.

After the prosthesis or wick has been fully compressed, as in FIG. 1, it should be suitably stored in a substantially moisture free environment until such time as it is to be used.

What is claimed is:

1. A method of fabricating an elongate, dehydrated, moisture-expandable prosthesis from a length of expanded, dehydrated, regenerated, cellulose sponge material, which comprises: forming the expanded, dehydrated, regenerated, cellulose sponge material into a hollow cylinder, the ends of which are connected together by the open bore extending axially through the hollow cylinder; applying radial compressive forces to the outer surface of the hollow cylinder to compact same and to reduce the diameter thereof without substantially altering its overall length; and substantially closing said open bore when said radial compressive forces are applied to said cylinder so that upon expansion, said cylinder will reassume a hollow configuration.

2. A method as called for in claim 1, wherein the reduction in diameter is from 30 to 80 percent.

3. A method as called in claim 1, wherein the outside diameter of the material prior to compression approximates 9 mm, and wherein the diameter after compression approximates 2 mm.

4. A method as called for in claim 1, wherein said material, prior to compression, is in the form of an elongate, hollow cylinder.

5. A method as called for in claim 1 which comprises the additional step of storing the compressed prosthesis in a moisture-free environment.

6. The method as called for in claim 5 further including a step of maintaining said compacted cylinder sufficiently rigid during storage for endwise insertion into a body opening without distortion or bending of said compacted cylinder.

* * * * *